United States Patent
Seo et al.

(10) Patent No.: US 10,689,614 B2
(45) Date of Patent: Jun. 23, 2020

(54) CELL CULTURE SUPPORT

(71) Applicant: AMOLIFESCIENCE CO., LTD., Seoul (KR)

(72) Inventors: In Yong Seo, Seoul (KR); Seung Hoon Lee, Paju-si (KR); Song Hee Koo, Seoul (KR); Ji Hyun Lee, Incheon (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 249 days.

(21) Appl. No.: 15/557,999

(22) PCT Filed: May 10, 2016

(86) PCT No.: PCT/KR2016/004851
§ 371 (c)(1),
(2) Date: Nov. 30, 2017

(87) PCT Pub. No.: WO2016/182300
PCT Pub. Date: Nov. 17, 2016

(65) Prior Publication Data
US 2018/0320129 A1    Nov. 8, 2018

(30) Foreign Application Priority Data

May 11, 2015  (KR) .......................... 10-2015-0065478

(51) Int. Cl.
*C12N 5/00* (2006.01)
*A61L 27/56* (2006.01)
*A61L 27/48* (2006.01)
*D04H 1/728* (2012.01)

(52) U.S. Cl.
CPC ................ *C12N 5/00* (2013.01); *A61L 27/48* (2013.01); *A61L 27/56* (2013.01); *C12N 2533/30* (2013.01); *C12N 2533/40* (2013.01); *C12N 2537/00* (2013.01); *C12N 2539/00* (2013.01); *D04H 1/728* (2013.01)

(58) Field of Classification Search
None
See application file for complete search history.

(56) References Cited

U.S. PATENT DOCUMENTS

2009/0148947 A1  6/2009  Perez et al.
2014/0363890 A1* 12/2014  Chun et al. .............. D01D 5/20
                                                          435/377

FOREIGN PATENT DOCUMENTS

| KR | 20070053443 | 8/2007 |
| KR | 20100039116 | 4/2010 |
| KR | 20100045158 | 5/2010 |
| KR | 20100045158 A * | 5/2010 |

OTHER PUBLICATIONS

Casasola, R. et al., Polymer 2014 vol. 55, pp. 4728-4737.*
Casasola, et al., Electrospun poly lactic acid (PLA) fibres: effect of different solvent systems on fibre morphology and diameter, Polymer, 2014, pp. 4728-4737.
International Search Report—PCT/KR2016/004851 dated Aug. 8, 2016.

* cited by examiner

*Primary Examiner* — Heidi Reese
(74) *Attorney, Agent, or Firm* — Cantor Colburn LLP

(57) ABSTRACT

Provided is a cell culture support, which is a support for attaching and culturing cells, and which includes: a fibrous web which is made by accumulating fibers of a biodegradable polymer and on which a plurality of pores are formed; and a plurality of beads formed on the fibers to secure spaces through which the cells penetrate into the fibrous web and grow therein.

4 Claims, 4 Drawing Sheets

CELL CULTURE SUPPORT

TECHNICAL FIELD

The present invention relates to a cell culture support, and more particularly, to a biodegradable polymer-based cell culture support which is capable of maximizing a cell survival rate by providing a culture environment familiar to cell culture, capable of transplant into the body after cell culture, and capable of being biodegraded and discharged outside the body after cell differentiation.

BACKGROUND ART

Recently, as the use of cultured cells for the treatment of diseases has expanded, interest and research on cell culture have been increasing.

Cell culture is a technique to collect cells from living organisms and cultivate the cells in vitro. Cultured cells are used to treat diseases by differentiating them into various tissues of the body such as skin, organs, and nerves.

Such cell culture requires a culture support to provide a culture environment similar to the body.

Cells cultured on the culture support grow in an adhering state, and improving adhesion of the cells to the culture support can increase the survival rate of the cells.

Therefore, research and development of new culture supports to improve adhesion of cells and to further optimize the culture environment of cells are continuously being carried out.

Korean Patent Laid-open Publication No. 2007-0053443 discloses a method of producing a support made of a sponge-shaped fiber having a three-dimensional structure by performing a process of electrospinning a fiber spinning undiluted solution, but fibers of the support have a thread shape of a predetermined diameter and pores of the support are defined as spaces existing between the fibers.

Therefore, it is difficult for the cells to penetrate into the support through the fine pores of the support to grow, and it is only possible to grow the cells in two dimensions, and there is a limit to the growth of the cells with the desired shape and skeleton.

DISCLOSURE

Technical Problem

The present invention has been made in view of the above-mentioned problems, and its object is to provide a cell culture support capable of maximizing a cell survival rate by providing a familiar and suitable environment for cell culture.

Another object of the present invention is to provide a biodegradable polymer-based cell culture support capable of facilitating cell culture, capable of assisting cell differentiation by transplanting cells in the body after cell culture, and capable of being biodegraded and excreted from inside of the body to outside of the body when the cell culture is completed.

Technical Solution

In order to accomplish the above object, there is provided a cell culture support, which is a support for attaching and culturing cells, according to an aspect of the present invention, the cell culture support comprising: a fibrous web which is made by accumulating fibers of a biodegradable polymer and on which a plurality of pores are formed; and a plurality of beads formed on the fibers to secure spaces through which the cells penetrate into the fibrous web and grow therein.

In the cell culture support according to one embodiment of the present invention, the biodegradable polymer may be one of PLA, PLLA, PGA, PLGA, PCL and PDO.

In the cell culture support according to an embodiment of the present invention, the fibers and the beads may include an additive for hydrophilic treatment.

In the cell culture support according to an embodiment of the present invention, the hydrophilic treatment additive may be one of Tween 80, Pluronic, and PVP.

In the cell culture support according to an embodiment of the present invention, the fibrous web may be a web obtained by electrospinning a spinning solution containing the biodegradable polymer and a solvent, and the spinning solution may have a viscosity of 50 to 2000 cps.

In the cell culture support according to an embodiment of the present invention, the diameters of the fibers may be 100 nm to 10 μm.

In the cell culture support according to an embodiment of the present invention, the diameters of the beads may be larger than the diameters of the fibers.

According to another aspect of the present invention, there is provided a cell culture support comprising: a first fibrous web made by accumulating first fibers having beads formed; a second fibrous web made by accumulating second fibers having beads formed in the first fibrous web; and a third fibrous web made by accumulating third fibers having beads formed in the second fibrous web.

In the cell culture support according to an embodiment of the present invention, the diameters of the second fibers may be smaller than the diameters of the first and third fibers.

In a cell culture support according to an embodiment of the present invention, the thicknesses of the first and third fibrous webs may be thinner than the thickness of the second fibrous web.

In the cell culture support according to an embodiment of the present invention, the fibers and the beads may be made of a biodegradable polymer.

In the cell culture support according to an embodiment of the present invention, the fibers and the beads may include an additive for hydrophilic treatment.

Advantageous Effects

According to the present invention, a cell survival rate can be maximized by implementing a cell culture support with a fibrous web having a structure most similar to an extracellular matrix (ECM) of the human body, thereby providing a familiar and suitable environment for cell culture.

According to the present invention, there is an advantage that it is possible to realize a cell culture support comprising a biodegradable polymer-based fiber support which can be cultured and then transplanted into the body to thereby assist cell differentiation, and which can be biodegraded and excreted from inside of the body to outside of the body when the cell culture is completed.

According to the present invention, there is an advantage that a cell culture support is embodied as a fibrous web made of a biodegradable polymer, and a plurality of beads suspended from the fibers of the fibrous web are formed to provide an enlarged space between the beads and the fibers and between the beads and the beads, so that the cultured cells can penetrate into the fibrous web to grow without distorting the shape and skeleton of the cells.

According to the present invention, a cell culture support is realized with a three-layered fibrous web structure to facilitate cell adhesion, to allow cells to penetrate into a laminated structure to grow, and to prevent the cells which penetrate into the laminated structure to grow from escaping to the bottom surface of the laminated structure, thereby providing a support on which cells can be grown with a desired shape and skeleton.

BEST MODE

Hereinafter, embodiments of the present invention will be described in detail with reference to the accompanying drawings.

According to an embodiment of the present invention, a cell culture support has a structural characteristic in which a fibrous web formed by accumulation of fibers of a biodegradable polymer obtained by electrospinning and composed of a plurality of pores is configured as a support for cell culture, and a plurality of beads are formed on fibers of the fibrous web so that cells to be cultured penetrate into the fibrous web to form a space to allow the cells to grow.

The biodegradable polymer-based cell culture support according to the embodiment of the present invention is a support having a three-dimensional structure capable of easily attaching cells and efficiently growing, and that can be transplanted without adverse effects in the body, and that can be differentiated into organs or internal organs of necessary function after transplantation into the body, to then be biodegraded.

Figure 1:
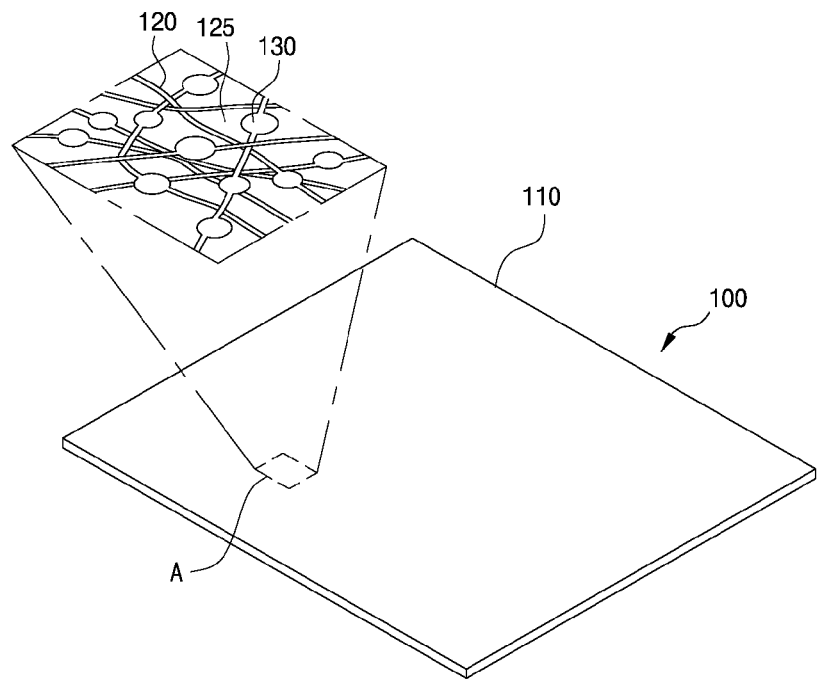
FIG. 1 is a perspective view for explaining a cell culture support according to the present invention.

Referring to FIG. 1, a cell culture support 100 according to the embodiment of the present invention is a support for attaching and culturing cells, and includes: a fibrous web 110 in which fibers 120 of a biodegradable polymer are accumulated and a plurality of pores 125 are formed; and a plurality of beads 130 formed on the fibers 120 to secure spaces for the cells to penetrate into the fibrous web 110 and grow therein.

When referring to an enlargement view of a region 'A' of a fibrous web 110 in FIG. 1, fibers 120 made of a biodegradable polymer are unevenly accumulated to form a flat plate type fibrous web 110, and a plurality of pores 125 between the accumulated fibers 120.

Here, the diameters of the fibers 120 are preferably 100 nm to 10 μm, and the fibers 120 are formed with a plurality of beads 130.

The diameters of the beads 130 are larger than the diameters of the fibers 120, and the beads 130 can be defined as an agglomerate of a biodegradable polymer. Here, at least one bead 130 is formed on each of all the fibers 120, or at least one bead 130 is formed on a part of all the fibers 120.

In some embodiments of the present invention, a biodegradable polymer and a solvent are mixed to prepare a spinning solution, the spinning solution is electrospun from a nozzle of a spinning apparatus to be described later to form a fiber 120 in which the bead 130 is suspended, and the fiber 120 is accumulates, to produce a fibrous web 110 for a cell culture support 100.

Here, in some embodiments of the present invention, the viscosity of the spinning solution in which the biodegradable polymer and the solvent are mixed is set to 50 cps to 2000 cps in order to realize the fibers having beads.

Here, if the viscosity of the spinning solution is less than 50 cps, the flowability of the spinning solution is high and the droplet is sprayed from the nozzle of the spinning apparatus. If the viscosity of the spinning solution exceeds 2000 cps, the amount of an organic solvent in the spinning solution becomes small, and thus the flowability of the spinning solution is low. In this case, only fibers are spun from the nozzle of the spinning apparatus.

The inventor(s) of the present invention confirmed through experiments that the formation of beads in the fibers 120 produced by electrospinning from the spinning nozzle is closely related to the viscosity of the spinning solution.

Figure 2A:
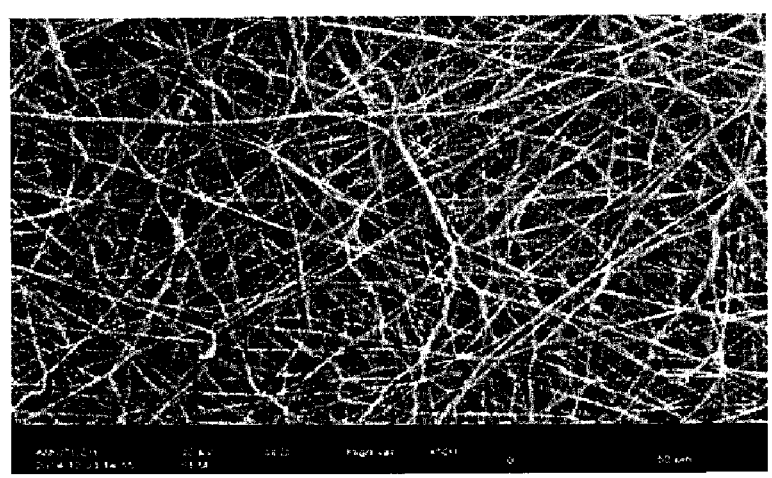
FIGS. 2A and 2B illustrate SAM photographs of fibrous webs according to the present invention.
Figure 2B:
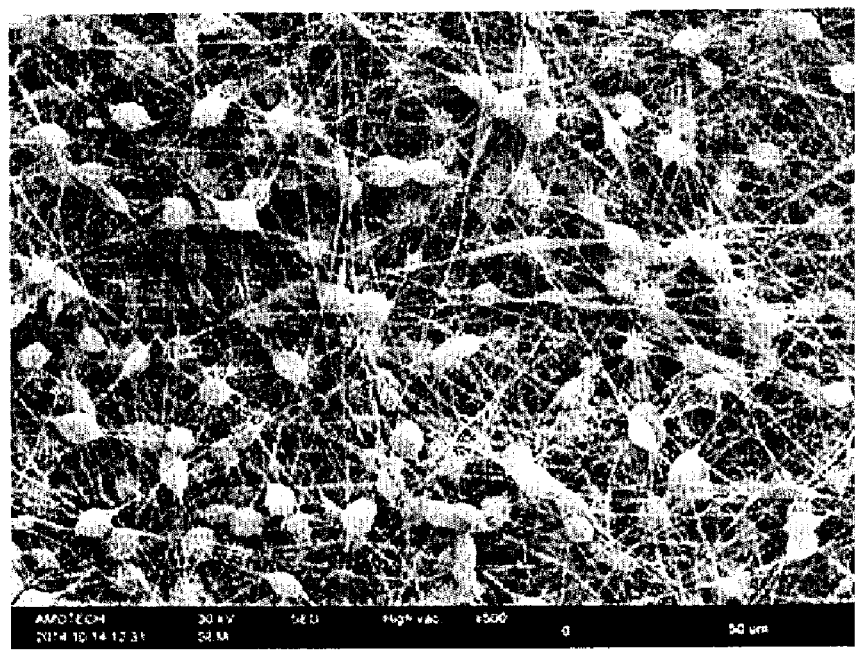
Figure 3:
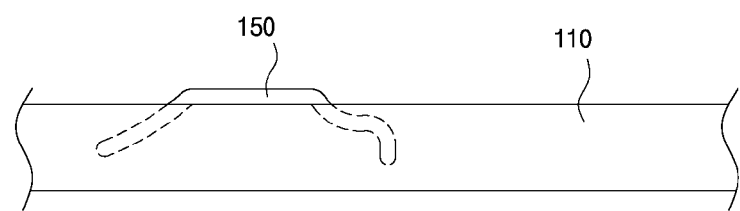
FIG. 3 is a view schematically showing a state in which cells growing inside the cell culture support according to the present invention are infiltrated.

That is, a biodegradable polymer was applied with a PLGA having a molecular weight of 130,000, and the PLGA and a solvent were mixed so as to have a viscosity of 2100 cps and electrospun. As a result, a fibrous web consisting of only fibers was produced as shown in FIG. 2A. However, the spinning solution in which the PLGA and the solvent were mixed was electrospun so as to have a viscosity of 260 cps in order to satisfy a viscosity range set in the embodiment of the present invention, to prepare a fibrous web in which fibers having beads were accumulated as shown in FIG. 2B.

Accordingly, in some embodiments of the present invention, the cell culture support is embodied as a fibrous web made of a biodegradable polymer, and a plurality of beads suspended from the fibers of the fibrous web are provided to form enlarged spaces (i.e. large pores) between a bead and a fiber, and between one bead and another bead. Accordingly, there is an advantage that the cells 150 cultured on the fibrous web 110 can penetrate into the fibrous web 110 and grow three-dimensionally.

That is, the fibrous web accumulated in the fibers only forms micropores between the fibers, but the fibrous web used as the cell culture support according to some embodiments of the present invention has pores between the bead and the fiber and between the beads. Therefore, the pores of the fibrous web according to some embodiments of the present invention in which beads are present become pores larger than the micropores formed between the fibers of the fibrous web in which beads are not present, and become spaces facilitating the penetration of the cells 150 to be grown.

In addition, a biodegradable polymer is defined as a polymer that is completely decomposed into water and carbon dioxide, or water and methane gas by microorganisms such as bacteria, algae, and fungi in nature. It can be said that a biodegradable polymer is plastic whose physical and chemical structure is changed by organic matter such as bacteria in the natural world, so-called rotten plastic.

In some embodiments of the present invention, a cell culture support made of a biodegradable polymer-based fiber support is realized so as to be capable of maximizing the survival rate of the cultured cells, assisting the differentiation of the cells after culturing the cells and transplanting them into the body, and being biodegraded and excreted from inside of the body to outside of the body when the cell culture is completed.

That is, in some embodiments of the present invention, a cell culture support capable of smoothly culturing cells and capable of being biodegraded by transplantation is embodied.

Here, since the fibrous web made of the accumulated fibers has the structure most similar to the extracellular matrix (ECM) of the human body, the support made of the fibrous web can provide a familiar and suitable environment for cell culture, to thereby maximize the survival rate of the cells.

The biodegradable polymer has a characteristic that the rate of biodegradation greatly varies depending on the type of the polymer. Since the degradation rate can be controlled according to the composition ratio of the polymer degrading relatively quickly and the polymer degrading relatively slowly. Accordingly, there is also an advantage that the rate of degradation of the cell culture support can be controlled according to the cell differentiation rate after the cell culture support that is obtained by culturing the cells is transplanted into the body.

In some embodiments of the present invention, a biodegradable polymer and a solvent are mixed to prepare a spinning solution, and an ultrafine fiber produced by electrospinning the spinning solution in an electrospinning apparatus to be described later is accumulated to prepare a cell culture support composed of a biodegradable polymer.

The biodegradable polymer may be one of PLA (Poly Lactic Acid), PLLA (Poly(L-lactic acid)), PGA (Poly(glycolic acid)), PLGA (Poly(lactide-co-glycolide)), PCL (Polycaprolactone) and PDO (1,3-Propanediol). The solvent may be at least one selected from the group consisting of DMAc (N, N-Dimethyl acetoamide), DMF (N, N-Dimethylformamide), NMP (N-methyl-2-pyrrolidinone), DMSO (dimethyl sulfoxide), THF (tetra-hydrofuran), EC (ethylene carbonate), DEC (diethyl carbonate), DMC (dimethyl carbonate), EMC (ethyl methyl carbonate), PC (propylene carbonate), water, acetic acid, formic acid, chloroform, dichloromethane, acetone and isopropylalcohol.

Meanwhile, in some embodiments of the present invention, in order to impart hydrophilicity to fibers and beads constituting a fibrous web of a cell culture support, a biodegradable polymer, an additive for hydrophilic treatment and a solvent are mixed to prepare a spinning solution, and the spinning solution is electrospun to accumulate fibers having beads having hydrophilicity to thereby produce a fibrous web.

Here, the additive for hydrophilic treatment may be one of Tween 80, Pluronic, and PVP.

The cell culture support is immersed in the culture solution, and the cells attached to the cell culture support grow by absorbing the nutrients in the culture solution. The cells can be well attached to a support having excellent hydrophilicity. Accordingly, according to some embodiments of the present invention, an additive for hydrophilic treatment is incorporated into the fibers and beads to thus realize a fibrous web having high hydrophilicity, to thereby provide an advantage of facilitating attachment of cells.

Figure 4:
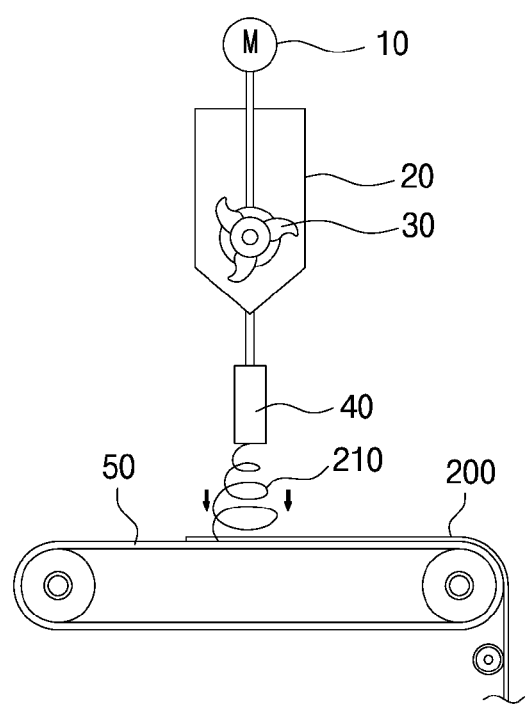
FIG. 4 is a schematic view illustrating an electrospinning apparatus for preparing a cell culture support according to the present invention.

FIG. 4 is a schematic view illustrating an electrospinning apparatus for preparing a cell culture support according to an embodiment of the present invention.

Referring to FIG. 4, an electrospinning apparatus for producing a cell culture support according to an embodiment of the present invention is characterized in that a stirring tank 20 for supplying a stirred spinning solution is connected to a spinning nozzle 40, a grounded collector 50 in the form of a conveyor that moves at a constant speed is placed in a lower portion of the electrospinning apparatus and spaced from the spinning nozzle 40, and the spinning nozzle 40 is connected to a high voltage generator.

Here, the biodegradable polymer and the solvent are mixed with a stirrer 30 to prepare a spinning solution. Here, a pre-mixed spinning solution may be used before being put into the electrospinning apparatus without mixing a biodegradable polymer and a solvent in the stirrer 30.

Thereafter, when a high voltage electrostatic force is applied between the collector 50 and the spinning nozzle 40, the spinning solution is spun by the spinning nozzle 40 into the ultrafine fibers 210 to then be emitted to the collector 50. The fibers 210 are accumulated to the collector 50 to form the fibrous web 200 of the cell culture support.

More specifically, the spinning solution discharged from the spinning nozzle 40 is discharged as the ultrafine fibers 210 while passing through the spinning nozzle 40 charged by the high voltage generator, and the ultrafine fibers 210 are sequentially laminated on the grounded collector 50 provided in the form of a conveyor moving at a certain speed to form the fibrous web 200 of the cell culture support.

Meanwhile, the cell culture support 100 according to some embodiments of the present invention can be realized as a laminated structure in which a plurality of fibrous webs 110 are laminated in which fibers of biodegradable polymers are accumulated and a plurality of beads are formed on the fibers.

Figure 5:
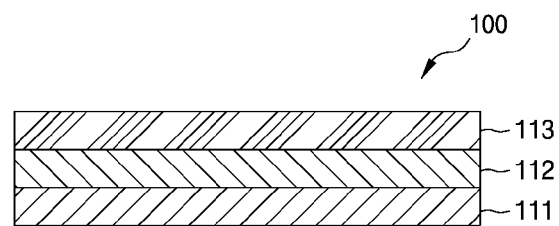
FIG. 5 is a cross-sectional view of a cell culture support laminated according to the present invention.

As an example, as shown in FIG. 5, the cell culture support 100 having a laminated structure may include a first fibrous web 111 made by accumulating first fibers having beads; a second fibrous web 112 made by accumulating second fibers having beads on the first fibrous web 111; and a third fibrous web 113 made by accumulating third fibers having beads on the second fibrous web 112.

In the cell culture support 100 having such a three-layer laminated structure, it is preferable that the second fibers have larger diameters than the first and third fibers.

That is, the third fibrous web 113 is laminated on the second fibrous web 112, and cells are attached to the third fibrous web 113 and cultured. Here, the diameters of the third fibers of the third fibrous web 113 are made smaller than the diameters of the second fibers of the second fibrous web 112, thereby widening the surface area to which the cells are attached so that the cells can be attached well.

Also, in some embodiments of the present invention, it is preferable that the thickness of each of the first and third fibrous webs 111 and 113 is thinner than the thickness of the second fibrous web 112.

The diameters of the second fibers of the second fibrous web 112 are larger than the diameters of the third fibers of the third fibrous web 113 and the space of the second fibrous web 112 is larger than the space of the third fibrous web 113, to thereby promote penetration of grown cells into the second fibrous web 112. The diameters of the first fibers of the first fibrous web 111 are less than the diameters of the second fibers of the second fibrous web 112 and the space of the first fibrous web 111 is narrower than the space of the second fibrous web 112 so that cells that penetrate and grow into the second fibrous web 112 are infiltrated into the first fibrous web 111 and can be prevented from growing on the bottom surface of the first fibrous web 111.

Therefore, the cell culture support 100 according to some embodiments of the present invention is realized in a structure in which the fibrous web is laminated in three layers, and thus there are several advantages of facilitating cell adhesion, allowing the cells to penetrate into the laminated structure and grow therein, preventing the cells infiltrated and grown into the laminated structure from escaping from the bottom surface of the laminated structure, so that the grown cells can have desired shapes and skeletons without being distorted.

Figure 6:
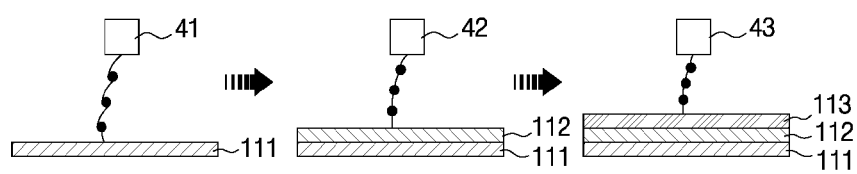
FIG. 6 is a schematic cross-sectional view for explaining a method of manufacturing a cell culture support having a laminated structure according to the present invention.

FIG. 6 is a schematic cross-sectional view for explaining a method of manufacturing a cell culture support having a laminated structure according to the present invention.

The cell culture support having a laminated structure is formed by accumulating fibers having beads discharged from first to third spinning nozzles 41, 42, and 43.

The spinning solution in which the biodegradable polymer and the solvent are mixed is supplied to the first to third spinning nozzles 41, 42 and 43 to discharge fibers having beads, and the first to third spinning nozzles 41, 42 and 43 are sequentially placed on the collector 50 moving at a constant speed of the above-described electrospinning apparatus.

First, after the first fibrous web 111 is formed by discharging the first fibers having beads from the first spinning nozzle 41, the first fibrous web 111 is moved to the lower portion of the second spinning nozzle 42. Then, the second fibrous web 112 is laminated on the first fibrous web 111 by discharging the second fibers having beads on the first fibrous web 111 by the second spinning nozzle 42.

Then, the second fibrous web 112 moves to the lower portion of the third spinning nozzle 43. Then, the third spinning nozzle 43 discharges the third fibers having beads on the upper portion of the second fibrous web 112, so that the third fibrous web 113 is laminated on the second fibrous web 112.

While the present invention has been particularly shown and described with reference to exemplary embodiments thereof, by way of illustration and example only, it is clearly understood that the present invention is not to be construed as limiting the present invention, and various changes and modifications may be made by those skilled in the art within the protective scope of the invention without departing off the spirit of the present invention.

INDUSTRIAL APPLICABILITY

The present invention is applied to a biodegradable polymer-based cell culture support capable of maximizing the cell survival rate by providing a culture environment familiar to a cell culture, capable of being transplanted into the body after cell culture, and capable of being biodegraded and discharged outside the body after cell differentiation.

What is claimed is:

1. A cell culture support comprising:
   a first fibrous web formed of first accumulated electrospun fibers, first pores, and first beads formed on the first accumulated electrospun fibers, the first beads securing spaces of the first pores;
   a second fibrous web laminated on the first fibrous web, the second fibrous web being formed of second accumulated electrospun fibers, second pores, and second beads formed on the second accumulated electrospun fibers, the second beads securing spaces of the second pores; and
   a third fibrous web laminated on the second fibrous web, the third fibrous web being formed of third accumulated electrospun fibers, third pores, and third beads formed on the third accumulated electrospun fibers, the third beads securing spaces of the third pores,
   wherein the third fibrous web is configured to culture cells adhered to the third accumulated electrospun fibers, and the second fibrous web is configured to grow the cells penetrated into the spaces of the second pores,
   wherein the third accumulated electrospun fibers have a diameter smaller than that of the second accumulated electrospun fibers to increase a surface area to which the cells are adhered, and
   wherein the first accumulated electrospun fibers have a diameter smaller than that of the second accumulated electrospun fibers to prevent the grown cells to penetrate into the first fibrous web from the second fibrous web, and
   wherein the first, second and third accumulated electrospun fibers are obtained by electrospinning a spinning solution having a viscosity from 50 cps to 2000 cps.

2. The cell culture support of claim 1, wherein the first and third fibrous webs have a thickness thinner than that of the second fibrous web.

3. The cell culture support of claim 1, wherein the first, second and third fibrous webs are made of a biodegradable polymer.

4. The cell culture support of claim 3, wherein the first, second and third fibrous webs include an additive for hydrophilic treatment.

* * * * *